United States Patent [19]

Schmidt-Ruppin et al.

[11] 4,318,926
[45] Mar. 9, 1982

[54] METHOD OF CURING OR ALLEVIATING HERPES INFECTIONS AND PHARMACEUTICAL COMPOSITIONS SUITABLE THEREFOR

[75] Inventors: Karl H. Schmidt-Ruppin, Arlesheim; Bohumir Lukas, Basel; Walter Wiesendanger, Münchenstein, all of Switzerland

[73] Assignee: Ciba-Geigy Corporation, Ardsley, N.Y.

[21] Appl. No.: 175,627

[22] Filed: Aug. 6, 1980

[30] Foreign Application Priority Data

Aug. 14, 1979 [CH] Switzerland ............... 7429/79

[51] Int. Cl.³ ............... A61K 31/135; A61K 31/445; A61K 31/40; A61K 31/33
[52] U.S. Cl. ............... 424/330; 424/267; 424/274; 424/244
[58] Field of Search ............... 424/330, 267, 274, 244

[56] References Cited

U.S. PATENT DOCUMENTS 3,399,201 8/1968 Schmidt et al. ............... 424/330

Primary Examiner—Jerome D. Goldberg
Attorney, Agent, or Firm—Prabodh I. Almaula

[57] ABSTRACT

Method for the treatment of herpes infections by administering a compound of the formula

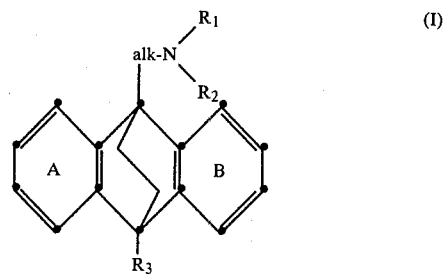

in which
alk represents alkylene containing 1 to 4 carbon atoms,
$R_1$ and $R_2$ independently of each other, represent hydrogen, alkyl containing 1 to 4 carbon atoms or together represent an alkylene radical containing 4 to 6 carbon atoms,
$R_3$ represents hydrogen, methyl or chlorine, and
the rings A and B, independently of each other, are unsubstituted or may be substituted by chlorine,
or their pharmaceutically acceptable acid addition salts, and also the pharmaceutical compositions suitable for use in this method.

7 Claims, No Drawings

METHOD OF CURING OR ALLEVIATING HERPES INFECTIONS AND PHARMACEUTICAL COMPOSITIONS SUITABLE THEREFOR

The present invention relates to a method of curing or alleviating herpes infections, and also to the pharmaceutical compositions suitable for use in this method.

It has been surprisingly found that compounds of the formula I

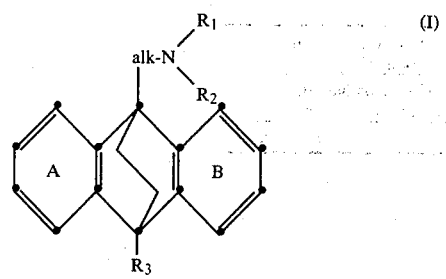

in which alk represents alkylene containing 1 to 4 carbon atoms, $R_1$ and $R_2$, independently of each other, represent hydrogen, alkyl containing 1 to 4 carbon atoms or together represent an alkylene radical containing 4 to 6 carbon atoms, $R_3$ represents hydrogen, methyl or chlorine, and the rings A and B, independently of each other, are unsubstituted or may be substituted by chlorine, and their pharmaceutically acceptable acid addition salts are highly effective on animals used for experimental purposes in experimental mucocutaneous and cutaneous herpes infections of the guinea-pig as well as in experimental Herpes encephalitis (inflammation of the brain) of the mouse.

The compounds of the formula I and their acid addition salts are described in U.S. Pat. No. 3,399,201. According to this patent specification, such compounds and their pharmaceutically acceptable acid addition salts act upon the central nervous system of mammals and can be used as active substances for medicines. From this information it could in no way be concluded that the compounds of the formula I and their pharmaceutically acceptable acid addition salts would be suitable for combating herpes infections.

In the compounds of the formula I, alk represents more especially trimethylene and above all methylene. $R_1$ and $R_2$ represent especially ethyl and propyl and more especially hydrogen and methyl, wherein above all $R_1$ represents hydrogen and $R_2$ simultaneously represents methyl. The rings A and B may be substituted independently of each other once or more times, but they are preferably substituted once and chlorine is present especially in the 2- or 3-position. However, especially preferred are compounds in which the rings A and B are unsubstituted. A compound preferably used as active substance is 9-[3-(methylamino)propyl]-9,10-dihydro-9,10-ethanoanthracene and more especially 9-[(methylamino)methyl]-9,10-dihydro-9,10-ethanoanthracene.

As pharmaceutically acceptable salts of the compounds of formula I there may be used, for example, the hydrochloride, hydrobromide, phosphate, ethanesulphonate 2-hydroxyethanesulphonate, acetate, lactate, malonate, succinate, fumarate. maleate, malate, tartrate, citrate, benzoate, salicylate, phenylacetate, mandelate or embonate and above all the methanesulphonate.

The antiviral activity of the pharmaceutical preparations of the invention can be assessed by animal experimentation, for example, by infection of the guinea-pig with Herpes genitalis caused by HVH 2/Angelotti with the treatment beginning 72 hours after infection (the stage of distinct symptoms), in connection with which reference is made to the procedures of B. Lukas et al., Arch Ges. Virusforsch. 44, 153–155 (1974) and 49, 1–11 (1975). For example, the strong activity of 9-[(methylamino)methyl]-9,10-dihydro-9,10-ethanoanthracene hydrochloride on oral administration is evident from Table 1(a) given below.

The occurrence of relapses after this treatment was strongly reduced (see Table 1(b)).

Intravaginal application twice a day of 0.1 ml of a gel of 0.1% strength of 9-[(methylamino)methyl]-9,10-dihydro-9,10-ethanoanthracene hydrochloride also caused a rapid regression of local symptoms of Herpes genitalis up to complete disappearance thereof.

In the Dermatitis herpetica produced by infection with HVH 1/Tup the treatment from 72 hours after infection with 5.0, 1.0 and 0.2 mg/kg p.o. (twice daily for 5 days) accelerated the retrogression of the skin lesions, as is apparent from Table 2.

In ascending vaginal infection of the guinea-pig, followed by paralysis and death, with $3 \times 10^3$ infectious units (PFU=plaque-forming units) of the especially neutropic strain HVH 2/Alabama, 9-[(methylamino)methyl]-9,10-dihydro-9,10-ethanoanthracene hydrochloride was equally effective (Table 3).

The prophylactic and early therapeutic peroral treatment increased the survival rate of mice after cerebral infection with $5 \times LD_{90}$ of HVH 1/Tup (Table 4.) From the percentage numbers of the surviving control animals it is observed that the infection was not equally strong in all the test groups. However, it can be seen from the results that when treatment starts before the infection the highest dosage of active substance has the same or a stronger action than lower dosages, whereas, when treatment starts later, according to test groups 3 and 4 the lowest dosage in relative terms had the strongest action.

TABLE 1a

Activity of 9-[(methylamino)methyl]-9,10-dihydro-9,10-ethanoanthracene hydrochloride in a blind experiment on guinea-pigs having Herpes genitalis caused by infection with HVH2/Ang.

| | | | Effect on local symptoms | | | | | | | | | | |
|---|---|---|---|---|---|---|---|---|---|---|---|---|---|
| | Dose | | Animals having at least 66% regression | | | | Animals having no symptoms | | | | | Animals | |
| Group | mg/kg p.o. | N | Day 4 | 7 | 9 | 11 | 9 | 11 | 14 | 18 | 25 | dead | paralysed |
| 1 | 5.0 | 20 | 2 | 7** | 11** | 14** | 5* | 8** | 9** | 12* | 15* | 0 | 2 |
| | | | | | | | x | x | | | | | |
| 2 | 1.0 | 20 | 0 | 11** | 15** | 16** | 10** | 16** | 16** | 17** | 20** | 0 | 0 |
| 3 | 0.2 | 20 | 1 | 10** | 14** | 15** | 8** | 9** | 12** | 15** | 17** | 0 | 0 |

TABLE 1a-continued

| | | | | | | | | | x | | | | |
|---|---|---|---|---|---|---|---|---|---|---|---|---|---|
| 4 | Placebo | 20 | 0 | 0 | 0 | 1 | 0 | 0 | 0 | 3 | 6 | 0 | 0 |

Treatment: twice a day for 5 days, starting on day 0, 3 days after the infection.

*$P<0.05$ } different from placebo
**$P<0.01$ }                          } Fisher Exact Test
x $P<0.05$  different from group 2 }
N = number of animals

TABLE 1(b)

The occurrence of relapses in Herpes genitalis in guinea-pigs after peroral treatment with 9-[(methylamino)methyl-9,10-dihydro-9,10-ethanoanthracene hydrochloride.

| | Number of animals[a] having relapses after days | | | | Number of animals having relapses of...days duration | | | | |
|---|---|---|---|---|---|---|---|---|---|
| Active substance and doasge | 28 | 60 | 90 | total | 7 | 14 | 21 | 28 | days |
| 3-[(methylamino)methyl]-9,10-dihydro-9,10-ethano-anthracene hydrochloride | | | | | | | | | |
| 5.0 mg/kg | 1 | | | 1 | | 1 | | | |
| 1.0 mg/kg | 0 | 0 | 0 | 0 | | | | | |
| 0.2 mg/kg | 1 | | 1 | 2 | 1 | 1 | | | |
| Placebo | 4 | 4 | 3 | 11[b] | 6 | 4 | 2 | 1 | |

N = 20 (see Table 1[a]
[a] without local symptoms for at least one preceding week.
[b] two of these with repeated relapses

TABLE 2

Activity of 9-[(methylamino)methyl]-9,10-dihydro-9,10-ethanoanthracene hydrochloride in guinea-pigs having Dermatitis herpetica caused by HVH 1/Tup.

| Active substance and dosage | Number of lesions[a] | Average area of the lesions on day 0[b] | Average area of lesions as a % of the area of day 0 | | | | | para-lysed animals |
|---|---|---|---|---|---|---|---|---|
| | | | 2 | 4 | 7 | 9 | 11 | |
| 9-[(methylamino)methyl]-9,10-dihydro-9,10-ethano-anthracene hydrochloride | | | | | | | | |
| 5.0 mg/kg p.o. | 12 | 86 mm² | 83** | 66** | 24 | 20 | 15 | 0/6 |
| 1.0 mg/kg p.o. | 12 | 97 mm² | 75** | 59** | 21 | 13 | 9 | 1/6 |
| 0.1 mg/kg p.o. | 12 | 96 mm² | 88** | 66** | 20 | 13 | 19 | 1/6 |
| control (dist. water) | 12 | 90 mm² | 122 | 103 | 66 | 45 | 25 | 3/6 |

| | | | Number of lesions with blisters/total number of lesions[c] | | | | | |
|---|---|---|---|---|---|---|---|---|
| 9-[(Methylamino)methyl]-9,10-dihydro-9,10-ethano-anthracene hydrochloride | | | | | | | | |
| 5.0 mg/kg p.o. | 12 | 12/12 | 1/12++ | 3/12++ | 0/12 | 0/12 | 0/12 | |
| 1.0 mg/kg p.o. | 12 | 12/12 | 6/12+ | 3/12++ | 0/12 | 0/12 | 0/12 | |
| 0.2 mg/kg p.o. | 12 | 12/12 | 1/12++ | 0/12++ | 0/12 | 0/12 | 0/12 | |
| control (dist. water) | 12 | 12/12 | 12/12 | 11/12 | 0/12 | 0/12 | 0/12 | |

Treatment: twice a day for 5 days starting on day 0, 3 days after the infection.
[a] two herpetic lesions on each of the 6 animals.
[b] day 0 = 100%.
[c] in the same test sequence as above.

*P 0.02 } Wilcoxon Rank Order Test
**p 0.005 }
+p 0.05 } Fisher Exact Test
++p 0.01 }

TABLE 3

Activity of 9-[(methylamino)methyl]-9,10-dihydro-9,10-ethanoanthracene hydrochloride in guinea-pigs, which have been infected intravaginally with HVH 2/Alabama.

| | | | | Effect | | | |
|---|---|---|---|---|---|---|---|
| Form of admini-stration | Dose mg/kg p.o. | N | start of treatment[b] after infection[a] | % survivors on day 35[c] | animals having no genital symptoms on day 14 | on day 21 | |
| Tablets[d] | 1.0 | 10 | 72 h | 30 | 30 | 30 | |

TABLE 3-continued

| (10 mg) | | | | | | |
|---|---|---|---|---|---|---|
| | 0.2 | 10 | 72 h | 50* | 40** | 50** |
| Placebo | — | 16 | — | 6 | 0 | 0 |
| Syrup | | | | | | |
| (1 mg/ml) | 1.0 | 18 | 48 h | 28 | 22 | 22 |
| | 0.2 | 15 | 48 h | 40** | 33 | 33 |
| Placebo | — | 14 | — | 0 | 0 | 0 |

[a]Infection with $3 \times 10^3$ PFU;
[b]Treatment: twice daily for 5 days;
[c]Deaths occured 10 to 14 dats after infection;
[d]dissolved in dist. water.
*Significant p <0.05 ⎫
**Significant p <0.01 ⎬ Fisher Exact Test.

TABLE 4

Activity of 9-[(methylamino)methyl]-9,10-dihydro-9,10-ethanoanthracene hydrochloride in mice that had been intracerebrally infected with HVH 1/Tup.

| Test group | Dose mg/kg[a] p.o. | N | Treatment time[b] | Survival of the animals[c] on day 17 in % B/K |
|---|---|---|---|---|
| | 1.0 | 14 | −2 h, twice daily, 5 days | 86/7** |
| | 0.3 | 14 | −2 h, twice daily, 5 days | 50/7* |
| 1 | 0.3 | 14 | +24 h, twice daily, 5 days | 57/7* |
| | 0.3 | 14 | +48 h, twice daily, 5 days | 29/7 |
| | 1.0 | 28 | −2 h, twice daily, 5 days | 32/0* |
| 2 | 0.3 | 42 | −2 h, twice daily, 5 days | 33/0** |
| | 0.1 | 42 | −2 h, twice daily, 5 days | 38/0** |
| | 1.0 | 42 | +24 h, twice daily, 5 days | 26/2* |
| 3 | 0.3 | 42 | +24 h, twice daily, 5 days | 26/2* |
| | 0.1 | 42 | +24 h, twice daily, 5 days | 50/2** |
| | 1.0 | 28 | +48 h, twice daily, 5 days | 11/7 |
| 4 | 0.3 | 28 | +48 h, twice daily, 5 days | 14/7 |
| | 0.1 | 42 | +48 h, twice daily, 5 days | 43/5* |

[a]Solution in phosphate buffer pH 7.4 (Sorensen) in test group 1. Solution in Aqua dist. in test groups 2, 3 and 4.
[b]Start of treatment before (−) and after (+) the infection.
[c]Treated/controls %, MF$_2$-females weighing 16–18 g.
*significant p <0.05 ⎫
**significant p <0.01 ⎬ Fisher Exact Test.

The compounds of the formula I and their pharmaceutically acceptable salts are therefore suitable for the treatment of herpes infections such as *Herpes genitalis*, *Herpes labialis*, Dermatitis and *Gingivostomatitis herpetica*, *Encephalitis herpetica*, *Herpes zoster* and Varicella.

In accordance with the invention, the compounds of the formula I and their pharmaceutically acceptable acid addition salts are administered, in the quantity necessary for curing or alleviating herpes infections and especially perorally, to warm-blooded creatures in need of treatment, alone or in combination with other pharmaceuticals.

The peroral dosage depends on the species of warm-blooded creature, the method of administration, the age and individual condition of the warm-blooded creature to be treated and is between about 0.01 and 5.0 mg/kg, preferably from 0.1 to 2.0 mg/kg, daily. In human medicine, the dosage also depends especially on the intensity of the symptoms and accordingly also on whether the above primary action can be accepted or is even desired. For adult persons of normal weight the individual doses are preferably between 2.5 and 10 mg administered three times of a compound of formula I or pharmaceutically acceptable acid addition salts thereof, the latter possibly being used in correspondingly higher doses if they are derived from acids having relatively high molecular weights. Correspondingly reduced or increased doses are administered to children or adults of low weight or to adults of high weight. Depending on the nature of the primary action, differing individual doses may be administered in the course of the day, which in the case of 9-[(-methylamino)methyl]-9,10-dihydro-9,10-ethanoanthracene having a tranquillising action at higher dosages or its pharmaceutically acceptable salts, such as the hydrochloride, are, for example, morning and midday 2.5 or 5 mg each and in the evening 5 or 10 mg.

Pharmaceutical compositions that may be used according to the invention in unit dose forms, such as dragées, tablets, capsules, suppositories or ampoules, contain an active substance preferably 2.5–25 mg, especially 2.5–10 mg, of a compound of the formula I or preferably a pharmaceutically acceptable acid addition salt thereof together with at least one pharmaceutical carrier substance. The active substances that may be used in accordance with the invention are also suitable for topical administration together with suitable pharmaceutical carrier materials.

Unit dose forms for peroral use contain as active substance preferably between 1% and 50% of a compound of formula I or a pharmaceutically acceptable acid addition salt thereof. For their production, the active substance is combined, for example, with solid, pulverulent carrier substances such as lactose, saccharose, sorbitol, mannitol, starches such as potato starch, maize starch or amylopectin, and furthermore laminaria powder or citrus pulp powder, cellulose derivatives or gelatine, if necessary with the addition of lubricants such as magnesium stearate or calcium stearate or polyethylene glycols, to form tablets or dragée cores. The dragée cores are coated, for example, with concentrated sugar solutions, which, for example, may furthermore contain gum arabic, talcum and/or titanium dioxide, or with a lacquer which is dissolved in easily fusible organic solvents or solvent mixtures. Colourants may be added to these coatings, for example to identify different doses of active substance.

As further unit dose forms for oral administration there are suitably dry-filled capsules of gelatine and also soft, closed capsules of gelatine and a plasticiser such as glycerine. The dry-filled capsules contain the active substance preferably in the form of a granulate, for example, in admixture with fillers such as maize starch, and/or lubricants such as talcum or magnesium stearate, and if desired stabilisers such as sodium metabisulphite ($Na_2S_2O_5$) or ascorbic acid. In soft capsules the active substance is preferably dissolved or suspended in suitable liquids such as liquid polyethylene glycols, and stabilisers may also be added.

As peroral forms of use that are not in unit dose form there may be considered syrups prepared in the usual manner, for example, those which contain the active substance or a pharmaceutically acceptable salt thereof dispersed therein at a concentration of from 0.05% to 0.25%, preferably together with the usual adjuncts such as polysaccharide or polyalcohols, for example, sorbitol, sweeteners and/or flavouring substances and preservatives, for example, an alkali metal sorbate.

As unit dose forms according to the invention for rectal use there may be considered, for example, suppositories which consist of a combination of an active substance with a suppository base substance. Suitable suppository base substances are, for example, natural or synthetic triglycerides, paraffin hydrocarbons, polyethylene glycols or higher alkanols. Also suitable are gelatine rectal capsules which consist of a combination of the active substance with a base material. Suitable base substances are, for example, liquid triglycerides, polyethylene glycols or paraffin hydrocarbons.

Ampoules for parenteral, especially intramuscular, administration contain preferably a water-soluble, pharmaceutically acceptable salt of the active substance, for example of 9-methylaminomethyl-9,10-dihydro-9,10-ethanoanthracene, in a concentration of preferably from 0.5 to 5%, if desired together with suitable stabilisers and buffers, in aqueous solution.

For parenteral, especially intravenous, administration infusion solutions, which contain, for example, a water-soluble pharmaceutically acceptable salt of the active substance, for example, in Sörensen phosphate buffer solution may also be considered, which, if necessary, may also be prepared immediately before use from an ampoule solution and this buffer solution or another infusion solution.

Pharmaceutical preparations for topical use are creams, ointments, gels, vaginal-ovula, pastes, foams, tinctures and solutions, which contain from about 0.1% to 1% of the active substance.

Creams are oil-in-water emulsions, which contain more than 50% of water. As oily bases there are used principally fatty alcohols, for example, lauryl, cetyl or stearyl alcohol, fatty acids, for example, palmitic or stearic acid, liquid to solid waxes, for example, isopropyl myristate, wool wax or bees wax, and/or hydrocarbons, for example, soft paraffins (petrolatum) or paraffin oil. Emulsifiers may be surface-active substances having predominantly hydrophilic properties, such as suitable non-ionic emulsifiers, for example, fatty acid esters of polyalcohols or ethylene oxide adducts thereof, such as polyglycerine fatty acid esters or polyoxyethylene sorbitan fatty acid esters, and also polyoxyethylene fatty alcohol ethers or polyoxyethylene fatty acid esters, or corresponding ionic emulsifiers, such as alkali metal salts of fatty alcohol sulphates, for example, sodium cetyl sulphate or sodium stearyl sulphate, which are normally used in the presence of fatty alcohols, for example, cetyl alcohol or stearyl alcohol. Additives to the aqueous phase are, inter alia, agents that decreases the rate at which the creams dry out, for example, polyalcohols such as glycerine, sorbitol, propylene glycol and/or polyethylene glycols, and also preservatives, perfumes, etc.

Ointments are water-in-oil emulsions, which contain up to 70%, but preferably from about 20% to about 50% of water or aqueous phase. The fatty phase may be especially hydrocarbons, for example, soft paraffins, paraffin oil and/or hard paraffin oil and/or hard paraffins, which for improving the water-binding ability preferably contain suitable hydroxy compounds such as fatty alcohols or esters thereof, for example, cetyl alcohol or wool wax alcohols, or wool wax. Emulsifiers are corresponding lipophilic substances, such as sorbitan fatty acid esters (spans), for example, sorbitan oleate and/or sorbitan isostearate. Additives to the aqueous phase are, among others, moisture-retaining agents such as polyalcohols, for example, glycerine, propylene glycol, sorbitol and/or polyethylene glycol, and also preservatives, perfumes, etc.

Fatty ointments are water-free and contain as a base especially hydrocarbons, for example, paraffin, soft paraffins and/or liquid paraffins, furthermore natural or partly synthetic fats, for example, coconut fatty acid triglyceride, or preferably hardened oils, for example, hydrogenated ground nut oil or castor oil, also fatty acid partial esters of glycerine, for example, glycerine mono- or di-stearate, and also, for example, the fatty alcohols mentioned in connection with the ointments and which increase the water-absorbing capacity, and emulsifiers and/or additives.

Pastes are creams and ointments having secretion-absorbing powder constituents such as metal oxides, for example titanium oxide or zinc oxide, and also talcum and/or aluminum silicates, which have the function of binding moisture or secretions present.

Gels are especially aqueous solutions of active substances in which gel formers, preferably those from the group of cellulose ethers such as, for example, methylcellulose, hydroxyethylcellulose or carboxymethylcellulose, or the vegetable hydrocolloids, such as sodium alginate, tragacanth or gum arabic, are dispersed and swollen up. Furthermore, the gels contain preferably also moisture-retaining agents of the group of polyalcohols, such as propylene glycol, glycerine and/or lower polyethylene glycols, and also wetting agents, for example, polyoxyethylene sorbitan fatty acid esters, such as polyoxyethylene sorbitan monolaurate. As further added substances the gels may contain the usual preservatives, for example benzyl alcohol, phenethyl alcohol, phenoxyethanol, p-hydroxybenzoic acid lower alkyl esters such as the methyl and/or propyl ester, sorbic acid or alkali metal salts thereof, or organic mercury compounds such as merthiolate.

Tinctures and solutions generally have an aqueous-ethanolic base, which contains, inter alia, polyalcohols such as, for example, propylene glycol or glycerine and/or lower polyethylene glycols, as moisture-retaining agents for reducing evaporation, and if necessary re-fatting substances such as fatty acid esters of lower polyethylene glycols, that is to say, lipophilic substances soluble in the aqueous-ethanolic mixture, as substitutes for the fatty substances withdrawn from the skin by the ethanol, and if desired further adjuncts and additives, besides the usual preservatives such as those mentioned above, and, for example, also the previously mentioned polyoxyethylene sorbitan fatty acid esters such as polyoxyethylene sorbitan monolaurate.

The manufacture of the pharmaceutical preparations for topical use is carried out in a manner known per se, for example, by dissolving or suspending the active substance in the base or, if necessary, at first in a part thereof. In working up the active substance as a solution it is generally dissolved in one of the two phases before emulsification; in working up in the form of a suspension the solid, preferably finely ground active substance, after being dispersed, is mixed with a part of the base and then added to the remainder of the base.

The preparations of the invention may contain, in addition to the usual preservatives, further biologically active, for example, antiphlogistically or antimicrobially active, such as antibacterially, antifungally or also antivirally active substances, for example Flumethasone, Neomycin, Gentamycin, lactic acid or Miconazole.

The topical preparations of the invention are suitable especially for the treatment of *Herpes genitalis, Herpes dermatitis* and *Herpes labialis*. For example, for the treatment of the first two, gels or ointments of the invention are applied, for example, by means of a tube or applicator 2 to 3 times daily, and for the treatment of *Herpes labialis* several times daily, to the affected parts of the body until the symptoms recede or until healing occurs. Aqueous solutions of the invention may be used, for example, for washing affected body cavities, especially for the treatment of *Herpes gingivostomatitis* or for the treatment of *Herpes keratoconjunctivitis*.

The following Examples describe the manufacture of typical forms of administration, but they in no way limit the scope of the invention.

EXAMPLE 1

100 g of 9-[(methylamino)methyl]-9,10-dihydro-9,10-ethanoanthracene hydrochloride are mixed with 202 g of lactose and 195 g of potato starch, the mixture is moistened with an alcoholic solution of 10 g of stearic acid and granulated through a sieve. After drying, 200 g of potato starch, 250 g of talcum, 3.0 g of magnesium stearate and 40 g of colloidal silicon dioxide are added, and the mixture is pressed to form 10,000 tablets, each weighing 100 mg and containing 10 mg of active substance, which, if desired, may be provided with dividing notches for finer adjustment of the dosage.

EXAMPLE 2

From 50.0 g of 9-[(methylamino)methyl]-9,10-dihydro-9,10-ethanoanthracene hydrochloride, 228.40 g of lactose and an alcoholic solution of 7.5 g of stearic acid a granulate is prepared, which, after drying, is mixed with 56.60 g of colloidal silicon dioxide, 200 g of talcum, 20 g of potato starch and 2.50 g of magnesium stearate and the mixture is pressed to form 10,000 dragee cores. These are then coated with a concentrated syrup of 417.3 g of crystalline saccharose, 6 g of shellac, 10 g of gum arabic, 0.2 g of colourant and 1.5 g of titanium dioxide and dried. The dragees so obtained each weigh 120 mg and each contains 5 mg of active substance.

Using 25.0 g of active substance and 253.40 g of lactose 10,000 dragees each containing 2.5 mg of active substance may be manufactured in an analogous manner.

EXAMPLE 3

To manufacture 1000 capsules each containing 10 mg of active substance, 10 g of 9-[(methylamino)methyl]-9,10-dihydro-9,10-ethanoanthracene hydrochloride are mixed with 263 g of lactose, the mixture is moistened uniformly with an aqueous solution of 2 g of gelatine and the mixture is granulated through a suitable sieve (for example, sieve III according to Ph. Helv. V). The granulate is mixed with 10 g of dried maize starch and 15 g of talcum and the mixture is charged uniformly into hard size 1 gelatine capsules.

EXAMPLE 4

A base substance for suppositories is prepared from 20 g of 9-[(methylamino)methyl]-9,10-dihydro-9,10-ethanoanthracene hydrochloride and 168.0 g of Adeps solidus and 100 suppositories are cast therewith each containing 20 mg of active substance.

EXAMPLE 5

0.100 g of 9-[(methylamino)methyl]-9,10-dihydro-9,10-ethanoanthracene hydrochloride, 0.100 g of crystalline saccharin-sodium, 40.000 g of sorbitol solution, 0.100 g of potassium sorbate, 0.500 g of citric acid monohydrate, 0.100 g of cherry flavouring and demineralised water up to 100 ml.

Preparation: The 9-[(methylamino)methyl]-9,10-dihydro-9,10-ethanoanthracene hydrochloride, crystalline saccharin-sodium, potassium sorbate and citric acid monohydrate and dissolved in cold demineralised water. Then the sorbitol solution and the cherry flavouring are added. Then the remaining demineralised water is added and the whole is vigorously mixed.

EXAMPLE 6

A solution of 25.0 g of 9-[(methylamino)methyl]-9,10-dihydro-9,10-ethanoanthracene hydrochloride in one liter of water is charged into 1000 ampoules and sterilised. One ampoule contains a 2.5% solution of 25 mg of active substance.

EXAMPLE 7

For the preparation of 5 liters of gel, 100 g of highly viscous carboxymethylcellulose are mixed with 500 g of propylene glycol and 3.25 ml of Aqua conservans and the mixture is allowed to swell to a homogeneous mucilage. Then a suspension of 50 g of 9-[(methylamino)methyl]-9,10-dihydro-9,10-ethanoanthracene hydrochloride in 1 liter of Aqua conservans is mixed in. Finally the mixture is increased to 5 liters with Aqua conservans, carefully mixed and the gel so obtained is charged into tubes. In this way a gel containing 1% of active substance is obtained.

Aqua conservans means an aqueous solution of 0.07% of p-hydroxybenzoic acid methyl ester (methylparaben) and 0.03% of p-hydroxybenzoic acid propyl ester (propylparaben).

What is claimed is:

1. A method for the treatment of herpes infections in warm blooded animals infected with said infections, which comprises administering to said animals a daily dose of an antiherpetically effective amount of a compound of the formula

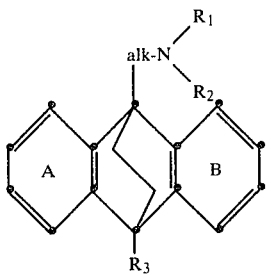

(I)

in which alk represents methylene or trimethylene, $R_1$ and $R_2$ independently of each other represent hydrogen or methyl, $R_3$ represents hydrogen and the rings A and B are unsubstituted, or a pharmaceutically acceptable acid addition salt of such a compound.

2. A method according to claim 1, characterised in that there is used as a compound of the formula I 9-(γ-methylaminopropyl)-9,10-dihydro-9,10-ethanoanthracene or a pharmaceutically acceptable salt thereof.

3. A method according to claim 2, characterised in that the hydrochloride is used as salt.

4. A method according to claim 1, characterised in that there is used as a compound of the formula I 9-[(methylamino)methyl]-9,10-dihydro-9,10-ethanoanthracene or a pharmaceutically acceptable salt thereof.

5. A method according to claim 4, characterised in that the hydrochloride is used as salt.

6. A method according to claim 1, characterised in that a compound of the formula I or a pharmaceutically acceptable acid addition salt of such a compound is administered to warm blooded animals in oral daily doses of 0.01 to 5.0 mg/kg.

7. A method according to claim 1, characterised in that the daily dose is from 0.1 to 2.0 mg/kg.

* * * * *